United States Patent
Lappalainen et al.

(10) Patent No.: US 6,614,041 B1
(45) Date of Patent: Sep. 2, 2003

(54) METHOD FOR DETERMINING THE WOOD/BARK RATIO FROM A FLOW OF WOOD MATERIAL

(75) Inventors: Timo Lappalainen, Jyväskylä (FI); Veli-Juhani Aho, Jyväsklä (FI); Ismo Nousiainen, Palokka (FI)

(73) Assignee: Metso Paper, Inc., Helsinki (FI)

( * ) Notice: Subject to any disclaimer, the term of this patent is extended or adjusted under 35 U.S.C. 154(b) by 0 days.

(21) Appl. No.: 09/914,586

(22) PCT Filed: Mar. 13, 2000

(86) PCT No.: PCT/FI00/00194
§ 371 (c)(1),
(2), (4) Date: Aug. 28, 2001

(87) PCT Pub. No.: WO00/54034
PCT Pub. Date: Sep. 14, 2000

(30) Foreign Application Priority Data

Mar. 11, 1999 (FI) .................................................. 990539

(51) Int. Cl.[7] .......................... G01N 21/86; B07C 5/342
(52) U.S. Cl. .......................... 250/559.08; 250/559.45; 250/223 R; 209/582
(58) Field of Search ........................ 250/559.04, 559.05, 250/559.07, 559.08, 559.1, 559.39, 559.4, 559.41, 559.45, 559.46, 226, 222.2, 223 R; 209/580, 581, 582, 587; 356/402, 407

(56) References Cited

U.S. PATENT DOCUMENTS 6,175,092 B1 * 1/2001 Binette et al. .............. 209/587

FOREIGN PATENT DOCUMENTS

| EP | 0831320 A2 | 3/1998 |
|----|------------|--------|
| WO | 0008448 A1 | 2/2000 |
| WO | 0025115 A1 | 4/2000 |

OTHER PUBLICATIONS

King et al., Using MORRPH in an industrial machine visionsystem, 1996, 18–26.

Lu et al., Machine vision system for color sorting wood edge–glued panel parts, 1997, 9–14.

Gunawardena et al., A spot–type defect detection and colour identification system for agricultural produce, 1991, 2531–2534.

* cited by examiner

Primary Examiner—Kevin Pyo
(74) Attorney, Agent, or Firm—Fildes & Outland, P.C.

(57) ABSTRACT

A method for determining the wood/bark ratio from a flow of wood material, in which the flow is illuminated in a non-flashing manner, scanned along a transverse line with a video camera with at least three channels, the line image corresponding to the line is digitalized into pixels each of which comprise intensity information, the intensity classes corresponding to the wood and the bark are determined in each channel and the pixels belonging to each class are calculated with the help of their intensity-information, and the wood/bark ratio is determined by the number of pixels situated in the different intensity classes. The dynamics of each channel are at least 10, most preferably 12 bit.

5 Claims, 1 Drawing Sheet

METHOD FOR DETERMINING THE WOOD/BARK RATIO FROM A FLOW OF WOOD MATERIAL

TECHNICAL FIELD

Figure 1:
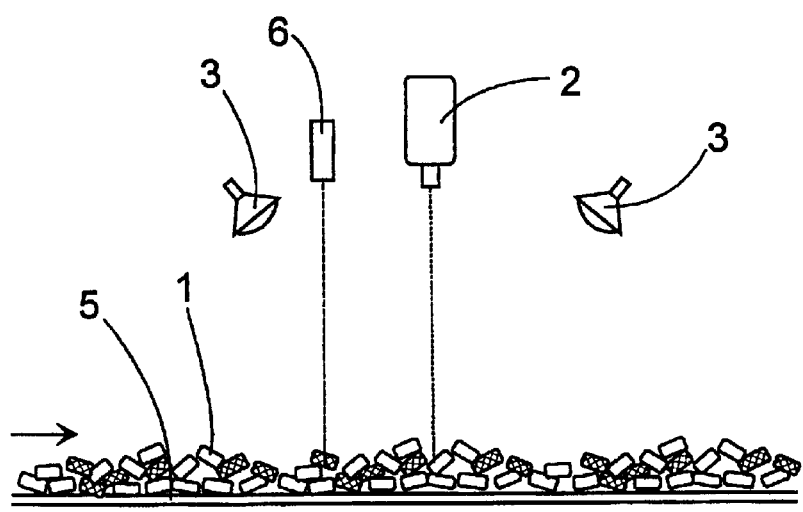

The invention relates to a method for determining the wood/bark ratio from a flow of wood material, in which the flow is illuminated, scanned along a transverse line with a video camera, the line image corresponding to the line is digitalized into pixels each of which comprise intensity information, the intensity classes corresponding to the wood and the bark are determined and the pixels belonging to each class are calculated with the help of their intensity information, and the wood/bark ratio is determined by the number of pixels situated in the different intensity classes.

BACKGROUND OF THE INVENTION

It is important to know the content of bark and wood in order to be able to peel the logs in an optimal way. By regulating the peeling process in such a way that the content of bark reaches the desired limiting values, it is on the one hand possible to avoid overpeeling and, on the other hand, possible to monitor the fulfilment of the quality requirements relating to the content of bark.

An on-line method for determining the wood/bark ratio from a flow of wood material has been presented in the publication of the application 831320 concerning a European Patent. In the said method the flow of wood material is scanned with a CCD line camera that is fixed in the direction transverse to the flow, in which there are 30–300 pixels/cm each of which measures the gray scale of the corresponding image field. The pixels are divided into main groups and subgroups are chosen from these main groups in which there exist at the most a chosen number (1–20) of adjacent pixels, the gray scale of which exceeds a set limit. The subgroups are filtered from the main groups and the average brightness is calculated for each completed group. The wood and the bark and possibly the background have been set their own classes of brightness, according to which each group is classed into its own class of brightness. The wood/bark ratio in the flow of wood is calculated on the basis of the pixels situated in each class. The method according to the publication is not very suitable for determining a wood chip flow that contains the bark of birches. The wood material of birches and the gray scales of the surface side of their bark are so close to each other that it is especially difficult to separate one from the other.

The Finnish patent 95511 presents a method for determining the differently colored surface areas from a flow of material, which is set to move forward on a transparent conveyor. Backgrounds in accordance with the partial colors are used in the many consecutive chambers, with which backgrounds each color is filtered in its turn. The color of the bark of trees differs somewhat, and the method is not well suited to determining the wood/bark ratio. Attention has not been paid to the effect of the layer height (height of the surface) to the survey results. The pieces of wood chips do not move on the conveyor as separate pieces but often as layers as thick as 20–50 cm. Furthermore, the wood chip and bark conveyors are not transparent.

Publication WO97/37780 presents a color separator, in which several images are taken with the help of an RGB color camera of the subjects to be classified and the images are turned into color shade and color saturation values, on the basis of which the classification is carried out. Scanning technology of 24 bit dynamics (3*8 bits) is utilized in the method, whereby in the color space of a specific yellow-brown area the color separating ability is not of a sufficiently good level for the color separation of wood and bark. In addition to this, 8 bit dynamics/channel has the problem that the sensor is easily saturated if an attempt has been made efficiently to take advantage of all the 256 gray scale values.

U.S. Pat. No. 5,887,073 presents a color separator in which pixels of set color are separated from a 3×8 bit RGB image into their own image. As above, there is here a low dynamics. In addition to this, intensity neutral color and color saturation color coordinates are used, but not at all any intensity information and the color response is not stabilized.

The invention relates to a method for determining bark and wood content. It is important to know the bark and wood content, so that the peeling of logs may be carried out in an optimal way. At the present time, the determining of the quality of wood chips is almost solely based on the taking of random samples, taken in different ways, and on the results achieved by the analysis of these samples. It is difficult to take a representative sample from a batch of wood chips. Furthermore, the taking of samples and especially the analyses are laborious and time consuming. It is not in practice possible to regulate the process with the help of the measurements, and the measurements only have meaning as a means of control. Continuously functional indicators based on gray scale CCD cameras are also available, but with them it is possible accurately to measure mainly the wood content on a bark conveyor. The determining of bark content on a wood chip conveyor is a much more demanding task, since the bark content to be measured is often 0.1–1.5%. The darkness of the bark of many kinds of wood makes the optical observation more difficult.

SUMMARY OF THE INVENTION

The object of this invention is to achieve an improved method for determining the wood/bark ratio in a flow of wood material. The characteristic features of the method according to the invention are presented in the adjoining patent claims. The changing of the black and white camera used in the method according to the EP-publication to a 24 bit color camera of the same level does not considerably improve the ability to separate, because it is difficult to recognize the color of the bark in a reliable manner and the color responses are not stable.

It is possible to improve the accuracy of the measurements to a considerable extent with the help of color information, when at the same time the dynamics (per channel) are improved to the level of at least 10 bits, most profitably 12 bits and the color responses are stabilized. It is then also essential to make the classification at least three-dimensionally. In order to achieve the best accuracy of the measurements, the color response needs to be stabilized.

The color stimulus $\Phi(Y)$ is some combination of the effect spectrum $(S(Y))$ and, depending on the subject, of the transmission $(T(Y))$, reflection $(R(Y))$ or radiance spectrum $(r(Y))$. When examining the wood or bark content by a CCD color camera technique it is a question of the reflection spectrum $(R(Y))$ of the surface. The values R, G and B of the color components are obtained as the scalar product of the color stimulus $\Phi(Y)$ and the sensitivity curves $r(Y)$, $g(Y)$ and $b(Y)$ of the red, green and blue components of the camera.

$$\begin{bmatrix} R \\ G \\ B \end{bmatrix} = \int \Phi(\lambda) \begin{bmatrix} r(\lambda) \\ g(\lambda) \\ b(\lambda) \end{bmatrix} d\lambda$$

The values (R, G and B) of the color components disclose the internal relations of the primary colors (blue, green and red) in the color mixture. In the method presented here the effect of the subject's change of brightness is minimized by calculating the relative shares of the color components r, g and b (r=R/(R+G+B), g=G/(R+G+B) and b=B/(R+G+B), whereby r, g and b are not dependant on the extent of the radiation power if the form of the spectrum of the source of light stays the same. This requirement is in practice fulfilled when the lights are not regulated in ways that would affect the color temperature of the source of light (no thyristor regulators are used) and the sources of light are allowed to stabilize for a time of sufficient length before starting the measurements (about 30 min).

The lighting must be non-flashing and its changes need to be compensated for. Non-flashing lighting may also be produced by synchronizing the scanning to the frequency of the lighting.

By taking advantage of the line camera technique, an even lighting of the subject may be achieved considerably more easily and more evenly than with the matrix camera technique. If the size of the scanned area is physically e.g. 600 mm×600 mm, when using a matrix camera it is necessary to illuminate the whole 600 mm×600 mm area evenly from the center of the area as well as from its edges. In the line camera technique it is enough evenly to illuminate a 600 mm wide area in the direction transverse to the conveyor but only about 1–2 mm in length. With the line camera, a chosen number of line images is taken one after the other from the moving flow. The consecutive lines are connected to one separate image usually already by the image card attached to the camera and an image matrix is achieved for further processing. Different image processing operations are performed on the image matrix. The most essential information from the point of view of the invention is contained in each separate line image. In order to achieve statistical reliability, a vast number of line images is included in the calculation.

In the method according to the invention the correction of the intensity has been achieved in two different ways: first, an rgb-image is calculated from the RGB image and, secondly, the intensity information of the chosen color channel (R or G) that corresponds well to the overall intensity is transformed with the help of a measuring of the height of the surface to intensity information that is independent of the layer height.

DETAILED DESCRIPTION OF THE INVENTION

The adjoining FIGURE presents a measuring arrangement according to the invention. The flow of material 1 moves from the left to the right in the figure e.g. by belt conveyor 5. The place that is to be scanned (the transverse line) is illuminated with lights 3 and the height of the wood chip surface at the place of scanning is measured with an indicator of the height of the surface 6 (e.g. an ultrasound measuring device, i.e. a US probe). The measuring is synchronized in accordance with the speed of the transporter. With the help of color line camera 2 a two-dimensional, digitalized image is obtained from the flow of wood material, when the consecutive line images are connected into the same matrix. A measuring of the height of the surface is advantageous, because the light intensity discerned by the camera drops in proportion to the square of the distance. Hereby the changes in the intensity in the RGB channels, caused by the changes in the layer height can be eliminated and also the intensity information of the subjects can be taken advantage of in the analysis.

The detailed stages of the method according to the invention are the following. The following example presents a three-channel solution. Several colour channels can be used in a corresponding manner.

1) The subject is illuminated with a non-flashing light (e.g. halogen lights or light sources provided with an electronic controlling unit).

1b) The measuring only takes place if according to the information received from the US probe the layer height is sufficient, whereby the transporter belt will not be visible on the wood chip conveyor.

2) The subject is scanned with a three-channel, most profitably 36 bit RGB line camera (12 bits/channel). When each probe has i pixels (e.g. 1000 pixels) and when a number equal to j (e.g. 600) consecutive lines is scanned, three image matrices (R-, G- and B-image matrices) of the size [i,j] are formed from the subject that is scanned.

3) The biases R0, G0 and B0 of the corresponding channels are deducted from the image matrices of each channel R, G and B. The biases have been predefined by measuring the gray scales of the channels at a time when no light is allowed to shine on the probe. The correction of the bias is a very important measure when determining the colour of dark subjects, when the measured colour coordinate is close to the bias value of the channel in question.

4) From the images (R, G and B) in which the bias has been corrected, the corresponding intensity neutral rgb-image matrices are calculated, in which r=R/(R+G+B), g=G/(R+G+B) and b=B/(R+G+B).

5) Each image point A(x,y) is classified as of the type bark or of the type wood in the rgb-space. For example an NN-classifier (nearest neighbor) can be used in the classification, whereby image point A(x,y) is classified as belonging to the class closest to which its rgb-coordinates are in some (normally Eucledian) geometry. It is noteworthy that bark and wood may have more than 1 class center. For example in the case of birch there can exist class centers both on the white bark and on the darker inner bark of the birch. The class centers are determined in advance by analysing known samples (such as is done in FIG. 4 of U.S. Pat. No. 5,887,073).

6) The intensity information of one of the channels the bias of which has been corrected (preferably R or G) is corrected with the help of a signal measured by a US probe, whereby it is possible also to take advantage of the intensity information of the subjects. In order to be able to take advantage of the intensity information it is necessary that the effect of the change of the layer height has been eliminated.

7) The points l(x,y) of the said intensity corrected matrix are classified according to the lightness of the pixel as either bark or wood. In the case of a wood chip conveyor, those points ate classified as bark for which the following is true:

If I(i,j)<T1 and I(i,(j−H))<T2 and I(i,j+H))<T2, then the subject is made up of bark.

Here T1 and T2 are set intensity criteria and H is the required transition criterion (e.g. 5). Now for T1 and T2, T1<T2 is true and with the help of H and T2 it is possible to fix the limits to the length and darkness of the subject. Those points for which the following is true are correspondingly accepted as wood on a wood chip conveyor:

If I(i,j)>T1 and I(i,j−H))>T2 and I(i,j+H))>T2, then the subject is made up of wood. Now T1>T2.

8) The classifications that have been carried out in the stages 5 and 7 are combined, whereby in the case of a wood chip line only those image points are accepted as bark that have been recognized as bark in both stages 5 and 7. Correspondingly in the case of a bark line only those points are accepted as wood that have been recognized as wood in both stages 5 and 7. Depending on the situation, it is possible to use some other condition.

9) The bark-% or the wood-% is calculated as the ratio of the classified pixels.

Shadows that are caused by the partial overlapping of the pieces of wood chips may cause lighting problems on a wood chip line, because the machine sight system may in some situations classify the shadows as bark. A method in which form information of the areas that are to be segmented may be used in the segmentation of the image in addition to the intensity information may be used to eliminate the effect of the shadows, i.e. a specific shape is required of the object in order for it to be accepted as a subject. In order to determine the form areas, the intensity matrix is graded with a grading method that takes into account the forms of the subject, and an additional requirement is set to the chosen class in the classification, stating that the form of a pixel that is to be placed in this class must belong to a form area that fulfills the criteria.

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

What is claimed is:

1. A method for determining the wood/bark ratio from a flow of wood material, in which the flow is illuminated in a non-flashing manner with a lighting having a color temperature, scanned along a transverse line with a video camera, the line image corresponding to the line is digitalized into pixels each of which comprise intensity information, the intensity classes corresponding to the wood and the bark are determined and the pixels belonging to each class are calculated with the help of their intensity information, and the wood/bark ratio is determined by the number of pixels situated in the different intensity classes, and at least three color channels are used the dynamics of which are each at least 10 bit and the classes are fixed at least three-dimensionally on these channels and three absolute color signals are produced, characterized in that the flow is illuminated in such a manner that the color temperature of the lighting is always kept stable and a bias correction is carried out to the absolute color signals R, G and B of a color probe by taking into account the response of the zero value of the actual light intensity of each channel and the absolute color signals are corrected to be relative by dividing the value of the absolute color signal of each channel with the sum (R+G+B) of the values of the signals of all channels.

2. Method according to patent claim 1, characterized in that a CCD color line camera is used as the camera.

3. Method according to patent claim 1, characterized in that an essentially unitary image area is scanned and a corresponding image matrix is formed and the corrections of the image and the classification of pixels are effected as matrix operations.

4. Method according to patent claim 1, characterized in that the gray scale value is measured as also the distance between the camera and the flow of wood material, according to which the gray scale value that is obtained is corrected and the pixels are classified into the chosen classes according to the chosen gray scale criterion and the wood/bark ratio is calculated in accordance with the chosen condition by using both the already mentioned at least three-channel classification and the gray scale classification.

5. Method according to patent claim 4, characterized in that an intensity matrix is formed from at least one relative color signal and a corrected intensity matrix is obtained by the gray scale value from the intensity matrix and forms of areas in the flow of wood material are recognized from the corrected intensity matrix, an additional criteria is set to the chosen class in the classification stating that a pixel that is to be placed in this class must belong to a form area that fulfills the criteria.

* * * * *